United States Patent
Wirix-Speetjens (10) Patent No.: US 7,217,561 B2
(45) Date of Patent: May 15, 2007

(54) METHOD FOR THE CONTROLLED TRANSPORT OF MAGNETIC BEADS

(75) Inventor: Roel Wirix-Speetjens, Maaseik (BE)

(73) Assignee: Interuniversitair Microelektronica Centrum (IMEC) vzw, Leuven (BE)

( * ) Notice: Subject to any disclaimer, the term of this patent is extended or adjusted under 35 U.S.C. 154(b) by 0 days.

(21) Appl. No.: 11/398,076

(22) Filed: Apr. 4, 2006

(65) Prior Publication Data

US 2007/0031980 A1    Feb. 8, 2007

Related U.S. Application Data

(62) Division of application No. 10/810,048, filed on Mar. 26, 2004, now Pat. No. 7,141,415.

(60) Provisional application No. 60/459,243, filed on Mar. 28, 2003.

(30) Foreign Application Priority Data

Mar. 28, 2003    (EP)    ................... 03447072

(51) Int. Cl.
C12M 1/34    (2006.01)
C12M 3/00    (2006.01)

(52) U.S. Cl. ................... 435/287.1; 204/155; 436/518; 436/523; 436/524; 436/525; 436/526

(58) Field of Classification Search ............... 204/155; 209/212–215, 225–227; 423/25; 429/10; 435/287.1; 436/518, 523–526
See application file for complete search history.

(56) References Cited

U.S. PATENT DOCUMENTS 4,021,790 A    5/1977 Aiken et al.
5,655,665 A * 8/1997 Allen et al. ............... 209/223.1
6,355,491 B1    3/2002 Zhou et al.
6,716,642 B1    4/2004 Wu et al.
6,949,355 B2 * 9/2005 Yamanishi et al. ........... 435/34
2002/0036141 A1    3/2002 Gascoyne et al.
2002/0048534 A1    4/2002 Storek et al.
2002/0048821 A1    4/2002 Storek et al.
2002/0076825 A1    6/2002 Cheng et al.
2002/0166760 A1    11/2002 Prentiss et al.

(Continued)

OTHER PUBLICATIONS

Lagae et al. On-chip manipulation and magnetization assessment of magnetic bead enxembles by integrated spin-valve sensors. Journal of Applied Physics (2002), vol. 91, No. 10, pp. 7445-7447.*

Deng, et al., "Manipulation of magnetic microbeads in suspension using micromagnetic systems fabricated with soft lithography", Applied Physics Letters, vol. 78, No. 12, pp. 1775-1777, (Mar. 19, 2001).

Reichel et al., "Atomic micromanipulation with magnetic surface traps," Physical Review Letters (1999), vol. 83, No. 17, pp. 3398-3401.

*Primary Examiner*—Long V. Le
*Assistant Examiner*—Leon Y. Lum
(74) *Attorney, Agent, or Firm*—Knobbe Martens Olson & Bear LLP (57) ABSTRACT

The present invention is related to a method for controlled transport of magnetic beads between a position X and different position Y, such that the magnetic beads are manipulated or transported by applying successively a series of N local magnetic fields which have magnetic field gradients different from 0 in the neighborhood of said magnetic beads. Each of these N local magnetic fields is generated by a single current carrying structure, in which the current density is not constant. The invention generally relates to application in the domain of biochips and micro-arrays, used in diagnostics, genetics and molecular studies.

25 Claims, 7 Drawing Sheets

U.S. PATENT DOCUMENTS

2002/0166800 A1   11/2002  Prentiss et al.
2003/0012693 A1    1/2003  Otillar et al.
2004/0018611 A1*   1/2004  Ward et al. .............. 435/287.2
2004/0142463 A1*   7/2004  Walker et al. .............. 435/325
2004/0262210 A1*  12/2004  Westervelt et al. ......... 210/222

* cited by examiner

METHOD FOR THE CONTROLLED TRANSPORT OF MAGNETIC BEADS

RELATED APPLICATIONS

This application is a divisional of U.S. patent application Ser. No. 10/810,048, filed Mar. 26, 2004, now U.S. Pat. No. 7,141,415, which claims priority to: (1) U.S. provisional patent application No. 60/459,243, filed Mar. 28, 2003, and entitled "METHOD FOR THE CONTROLLED TRANSPORT OF MAGNETIC BEADS AND DEVICES FOR THE METHOD;" and (2) European Application No. EP 03447072.4, filed Mar. 28, 2003.

Each of the above-referenced patent applications is hereby incorporated by reference in its entirety.

BACKGROUND OF THE INVENTION

1. Field of the Invention

The present invention is related to the field of microelectronic devices, designed to transport and manipulate magnetic beads on chip. Application domains are biochips, biosensors, diagnostics, genetics and molecular studies.

2. Description of the Related Art

Following the publication of the first draft of the human genome sequence, the next major task is to determine the function that each of the genes (i.e. >35,000) have in each of the tissues in the body over a range of environmental conditions. Using arrays of thousands of probes which are specific to individual genes, DNA microarrays enable the extent to which individual genes are switched on or off to be determined. Genetic variation among individuals also contributes to variation in the way genes behave in response to changes in the environment. Simultaneous detection of variation at thousands of locations (i.e. single nucleotide polymorphisms or SNPs) in the genome can also be achieved using DNA microarray technology. Applications of DNA microarrays therefore include gene expression profiling, gene sequencing, gene discovery, and genotyping, for users in healthcare, academia and the pharmaceutical and biotechnology industries. Currently the major factors limiting the uptake of DNA microarray technology include low sensitivity, the high cost of the technology, requirement for specialist operators and throughput.

Electronic biochips have the potential to overcome these limitations. Here, exploitation of state-of-the-art micro- and nano-technology design, fabrication and characterization tools and processes enable development of devices and systems that can interface directly with biological reactions. A possibility involves combining magnetic bead-based bioassays with magnetic sensor technology. From a biotechnology perspective, paramagnetic beads (e.g., 0.05–10.0 □m diameter) are available commercially from a number of sources with a range of surface functional chemistries, for well established applications including isolation and transportation of nucleic acids, proteins and whole cells. In microelectronics, GMR-based magnetic sensors have provided an enabling technology for memory applications. Thus, integration of paramagnetic bead-based nucleic acid assays on a functional biochip surface incorporating magnetic sensors, provides the basis for a range of biochip platforms.

Next to the detection of the magnetic beads, the transport and manipulation of beads is a limiting factor, which has to be taken into account in biochip designs and methods.

In the past, systems have been described for the manipulation of magnetic microbeads based on permanent or electromagnets with dimensions >5 mm, which did not allow for magnetic fields localised over microscale regions.

Commercial devices exist for sorting and separation of magnetic microbeads, but they have a limited capability of performing complex manipulations of these beads since they make use of permanent magnets or electromagnets.

In Whitesides et al., "Manipulation of magnetic microbeads in suspension using micromagnetic systems fabricated with soft lithography", Applied Physics Letters [Vol 78, Nr 12 Mar. 19, 2001, pages 1775–1777] and US2002/0166800, systems are described comprising current carrying wires that can generate strong local magnetic field gradients, which in their turn can control the position of magnetic microbeads in aqueous suspension.

SUMMARY OF THE CERTAIN INVENTIVE ASPECTS

It is an aim of various inventive aspects to provide a novel method and corresponding devices for the manipulation and transportation of magnetic beads on chip. Inventive aspects generally point to application in the domain of biochips and microarrays, used in diagnostics, genetics and molecular studies, but can be applicable whenever there is a need of performing nanoscale or microscale transport.

In one embodiment, the invention provides a method for the controlled transport of magnetic beads between a position X and different position Y along a path P is disclosed, wherein the magnetic beads are manipulated or transported by applying successively a series of N local magnetic fields which have magnetic field gradients different from 0 in the neighbourhood of the magnetic beads.

Magnetic beads are known in the art and can have sizes between 50 nm and 10 µm. Preferably the magnetic beads have sizes between 100 nm and 5 µm. Preferably the magnetic beads are suspended in a fluid.

For the purpose of this invention the term 'local magnetic field' may be understood as the magnetic field which is essentially felt by the magnetic bead. Technically other magnetic fields can be generated at the same time when the local magnetic field is generated, but then they have to be sufficiently spatially separated from the bead. Possibly at least one of these contemporary fields may become a local magnetic field later in the controlled transport process according to the present invention.

In preferred embodiments aimed at the application areas of biochips, biotechnology, diagnostics, genetics and molecular studies the magnetic beads are attached to biological or chemical specimen. Also possible is that biologic or chemical specimen already carry a magnetic moment and coupling to a magnetic bead is not anymore necessary; seen in another way, the biological or chemical specimen can have an integrated magnetic bead.

Preferably the local magnetic field is essentially spread over an area which has dimensions of the order of 5 to 50 times the size of the bead or group of beads. More preferably the local magnetic field is essentially spread over an area which has dimensions of the order of 10 to 40 times the size of the bead or group of beads. A group of beads localized at a location of minimal energy in a magnetic field can have different spatial distributions, induced by the shape of the field. An indicative but not necessarily precise measure for the size of a group of beads can be the distance between begin and end of the group, measured along the current direction. A specific group of beads can thus be defined as a cluster of beads for which each bead is attracted to the same physical location of minimal energy at a given time.

Preferably the application of the local magnetic field is long enough to allow the magnetic bead to move to the location of its lowest energy in the local magnetic field (L_E_min). Embodiments wherein the time of application of the local magnetic field is shorter then the time necessary to allow the magnetic bead to move to the location of its lowest energy in the local magnetic field are also possible, but at the moment of switching to the next local magnetic field, the bead in that case reaches the influence area of the next local magnetic field such that it is attracted towards the location of its lowest energy in this next local magnetic field.

An aspect of the present invention is that each of the local magnetic fields, which have a gradient different from 0 in the neighborhood of said magnetic bead, is generated by a single current carrying structure.

These current-carrying structures can be created by standard state-of-the-art microelectronic process technology.

The series of N successive local magnetic fields can be generated by M current carrying structures.

Each of these current-carrying structures has a non-constant charge current density in order to achieve a gradient different from 0 in the neighborhood of said magnetic bead.

The non-constant charge current density can be generated by varying the shape of the cross-section of the current-carrying structure.

The non-constant charge current density can be generated by varying the cross-section surface area of the current carrying structure.

The non-constant charge current density can be generated by varying the width of the current carrying structure along the current direction.

The series of N locations of lowest energy (L_E_min {i}, with i between 1 and N) of the magnetic beads, corresponding to the series of N local magnetic fields, defines a predefined path.

In a preferred embodiment M equals 2 and the local magnetic fields are generated alternately in each of the current conducting structures.

Preferably current carrying structures have a periodic shape, formed by repeating a basic structure element.

Preferably this basic structure element has no mirror symmetry with respect to an axis which is orthogonal to the current direction.

Preferably the cross-section surface area is decreasing when going from 1 side of the basic structure element to the other side of the basic structure element, along the current direction.

In a preferred embodiment the current carrying structures are isometric.

In a preferred embodiment the current carrying structures are positioned above each other, being shifted over a distance different from 0 along the current direction.

In another preferred embodiment the current carrying structures are positioned next to each other such that their respective current directions are parallel and wherein both structures are shifted over a distance different from 0 along the parallel direction.

Advantageously the shifted distance equals half the length of the basic structure element.

In a preferred embodiment the basic structure element is sharkfin-like or triangular-like or sawtooth like.

The method according to various inventive aspects can be used in detection schemes for biological or chemical specimen, wherein the controlled transport of biological or chemical specimen is important. The method and devices according to the present invention provide such a controlled transport and mobility of beads and thus test specimen and consequently provides for a new range of new biochip-test schemes; for instance test specimen can be transported towards and from predetermined testing areas on chip.

The method and corresponding devices according to the present invention can be applied on a cluster or group of magnetic beads, whereby isolation, alignment and sequencing of magnetic beads is achieved due to the limited spatial resolution of the predetermined path compared to the bead size. These properties can be advantageously used in lab on chip design and analysis methods. They allow for instance the bead per bead—and consequently per one biological or chemical specimen based transport or manipulation. A demonstration of this bead per bead transport is for instance shown in FIG. 3, FIG. 4 and FIG. 7, where the individual beads (corresponding to dark spots in the figures) can be clearly indicated.

BRIEF DESCRIPTION OF THE DRAWINGS

FIGS. 1a and 1c are top views. FIGS. 1b and 1d are cut-views along respectively the lines B–B' and C–C'.

FIG. 3 is a picture of a practical realization of a preferred embodiment of the present invention, corresponding to FIG. 1a.

DETAILED DESCRIPTION OF CERTAIN INVENTIVE EMBODIMENTS

Movement of magnetic beads in a 1-dimensional way is achieved by applying a magnetic force:

$$\vec{F} = \vec{\nabla}(\vec{M} \cdot \vec{B})$$

Figure 1A:
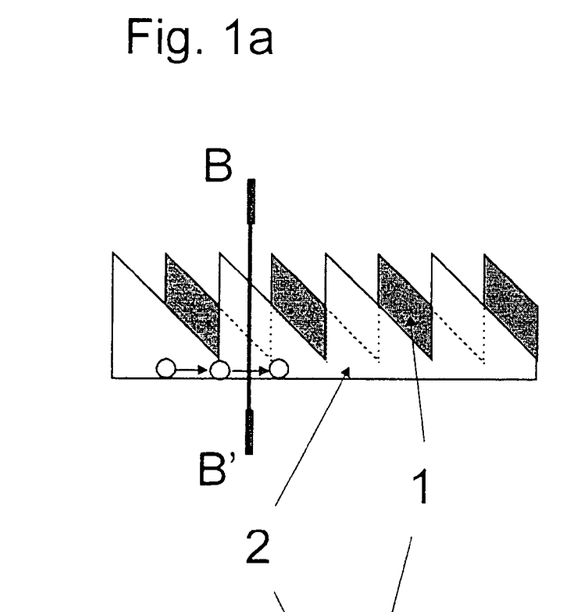
FIGS. 1a and 1b illustrate a preferred embodiment of the present invention for which the fabrication comprises 2 metallisation steps ((1)+(2)).
Figure 1B:
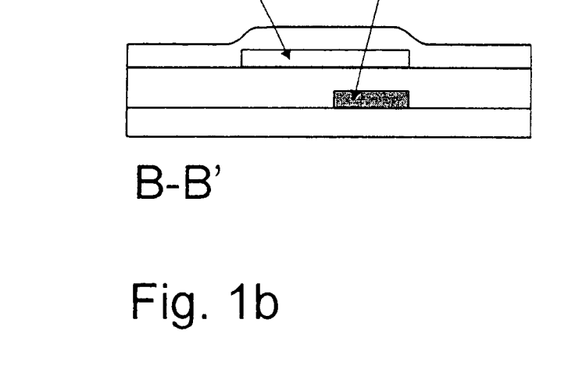
Figure 1C:
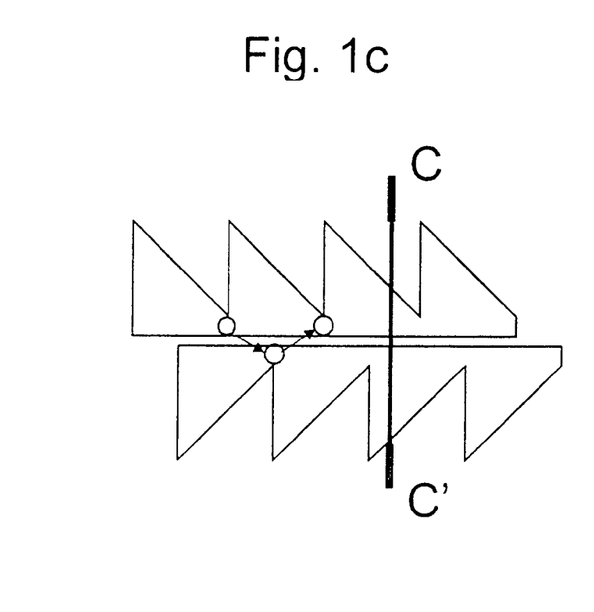
FIGS. 1c and 1d illustrate a preferred embodiment of the present invention for which the fabrication comprises 1 metallisation step.
Figure 1D:
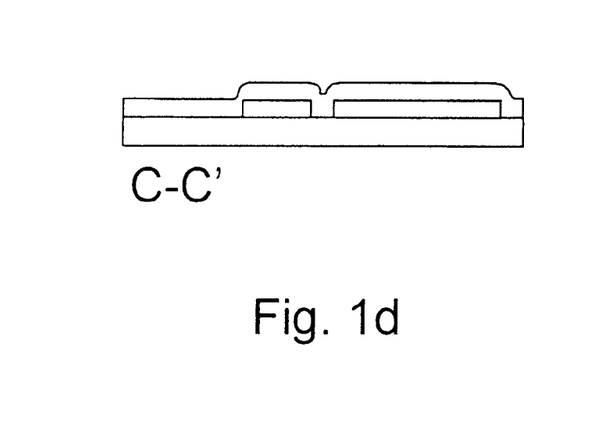
Figure 2A:
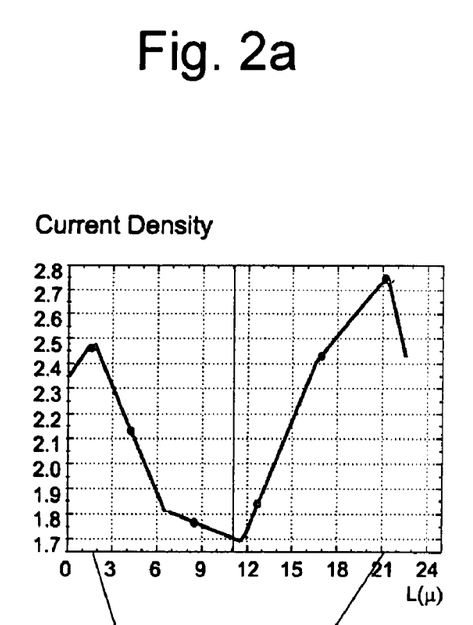
FIG. 2a and FIG. 2c are showing the evolution of the current density in function of the longitudinal position in the basic structure element. The current densities in FIG. 2 are in arbitrary units.
Figure 2B:
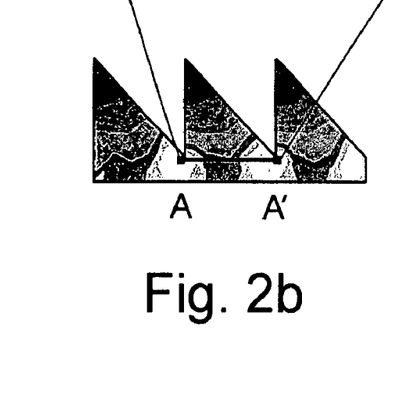
FIGS. 2b and 2d illustrate 2 current carrying structures according to an embodiment of the current invention, wherein the 2 current carrying structures differ by a difference in the length (A–A', B–B') of the basic structure element.
Figure 2C:
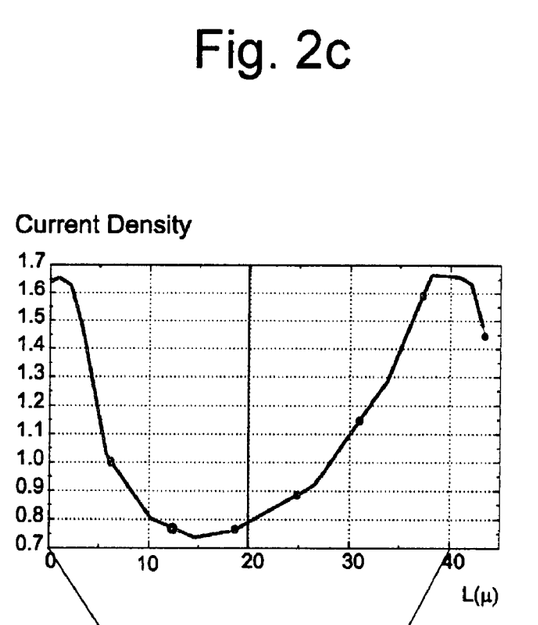
Figure 2D:
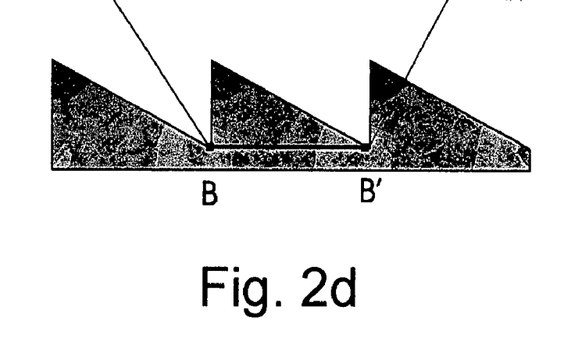
Figure 3:
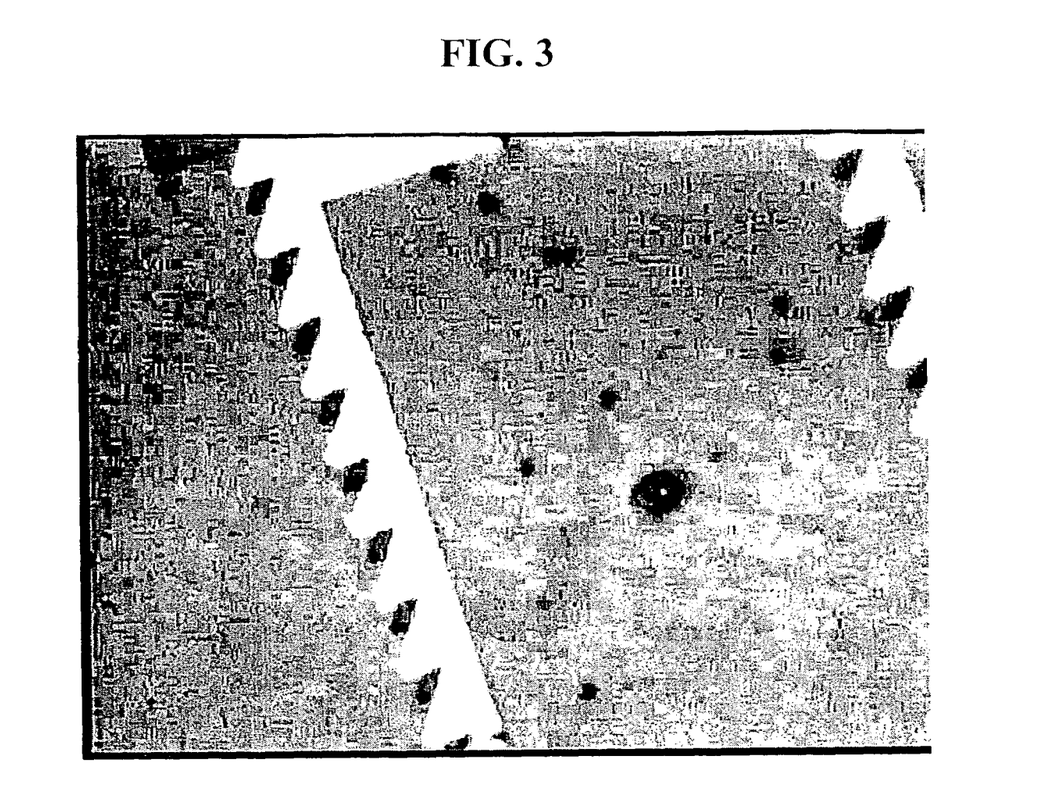
Figure 4:
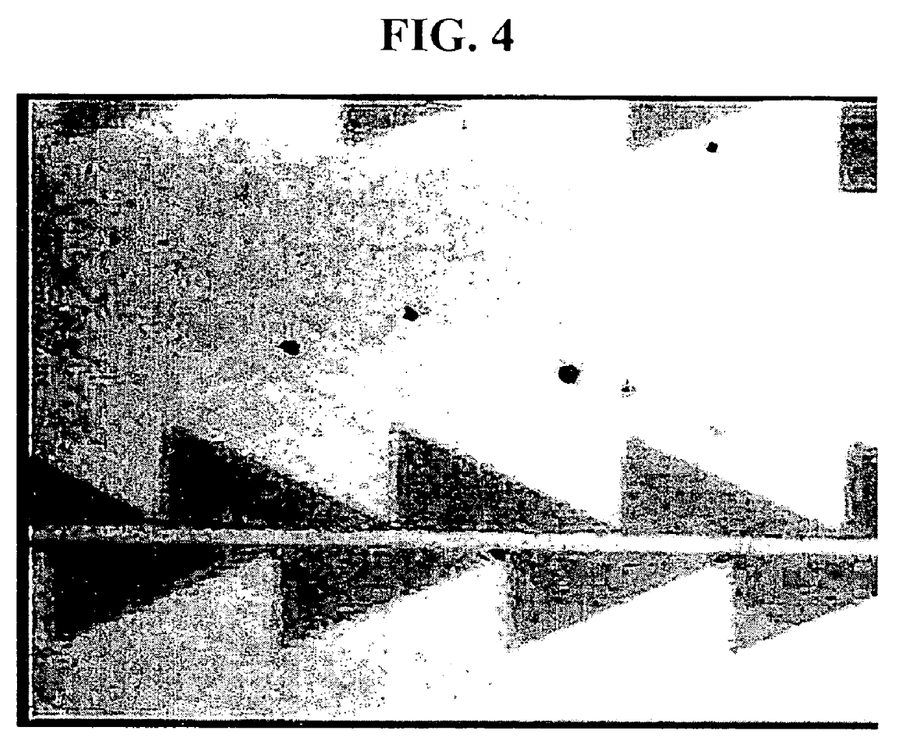
FIG. 4 is a picture of a practical realization of a preferred embodiment of the present invention, corresponding to FIG. 1c.

Such a magnetic force can thus be generated by both magnetizing the super-paramagnetic bead and creating a magnetic field gradient. On-chip field generation lines can create both. FIGS. 1a–b (can be fabricated using 2 metallisation steps) and FIGS. 1c–d (can be fabricated using a single metallisation step) show structures that are able to form a magnetic field gradient and hence are able to pull a magnetic bead towards the smallest width of the conductor or current carrying structure. Pictures of the corresponding real examples are depicted in FIGS. 3 and 4. As can be derived from FIGS. 2a–b (basic elementary structure corresponding to a length of 20 μm and a width of 20 μm) and FIGS. 2c–d (basic elementary structure corresponding to a length of 40 μm and a width of 20 μm), the structures can be characterized in that they generate a magnetic field gradient different from 0 because their current density within each basic structure element is not constant. These structures have a periodically repeating basic structural element. In this case the basic structural element is sharkfin-like, but this can also be triangular (double-sharkfin), sawtooth-like or can have other shapes. By shifting a second conductor half a period from the first, magnetic beads can be moved in a peristaltic way from one minimal width to another. This occurs by switching alternating DC currents through the conductors. For the given examples of current carrying structures a magnetic bead size of the order of 2 μm can be preferred.

Preferably both conductors behave magnetically in a similar way. In order to do this, for instance a first metallisation [TiW (10 nm)/Au (150 nm)/TiW (10 nm)] can be deposited on the substrate, which can be followed by a passivation layer Si3N4 [500 nm]. To start with a flat surface, a CMP step flattens the topography, keeping a certain thickness of the Si3N4 to isolate both conductors. The second metallisation can be deposited in exactly the same way as the previous one, again followed by a passivation layer. In this way, both conductors have the same current distribution and hence the same magnetic behaviour. Other planarisation steps, such as Spin on glass (SOG) or damascene process technology can replace the Chemical Mechanical Polishing (CMP) step.

A coplanar transporting device was fabricated using standard semiconductor fabrication and photolithography techniques onto Si substrates with 300 nm thermal SiO2. The current conductors (TiW 10 nm,/Au 150 nm,/TiW 10 nm) were evaporated and patterned using a lift off process. Polyimide was then spun onto the substrates as a passivation layer. After spinning, the polyimide was cured at 350° C. for 20 minutes. Finally, contact paths were opened to the conductors and the device was packaged in such a way as to allow the magnetic particle fluid to be dispensed onto the chip's surface.

For the stacked conductor device (see FIG. 1A), it is preferred to planarize the surface on top of the first conductor prior to the deposition of the second, to make both conductors behave magnetically in a similar way. Polyimide was used for this planarization step after which a second current conductor was deposited. Finally, a second polyimide layer was spun onto the substrates to act as a passivation layer and contact paths were opened to the conductors.

Currents have been applied of up to 100 mA through the magnetic field generating current conductors by means of a current source, and a switching means to switch the current source between both conductors was applied.

A PC was used to control the current value and the switching frequency. A CCD camera was used for optical monitoring of the movement of the magnetic particles.

Beads with a very uniform size distribution were used for the experiments, which contain 15% magnetite $Fe_2O_4$ in a dextran matrix to form regularly shaped particles with a diameter of 2 microns. These particles can be coated with covalently bound biological agents such as DNA and proteins, without significantly changing the behavior of the particles. The particles were suspended in water (other liquids are of course possible), with a magnetic particle density of around 0.0625 mg/ml. A volume of 3 μl was used for each experiment. As soon as the currents are applied, the magnetic beads become magnetized and start to move towards the current line edges, driven by the gradient in the magnetic field.

Figure 7:
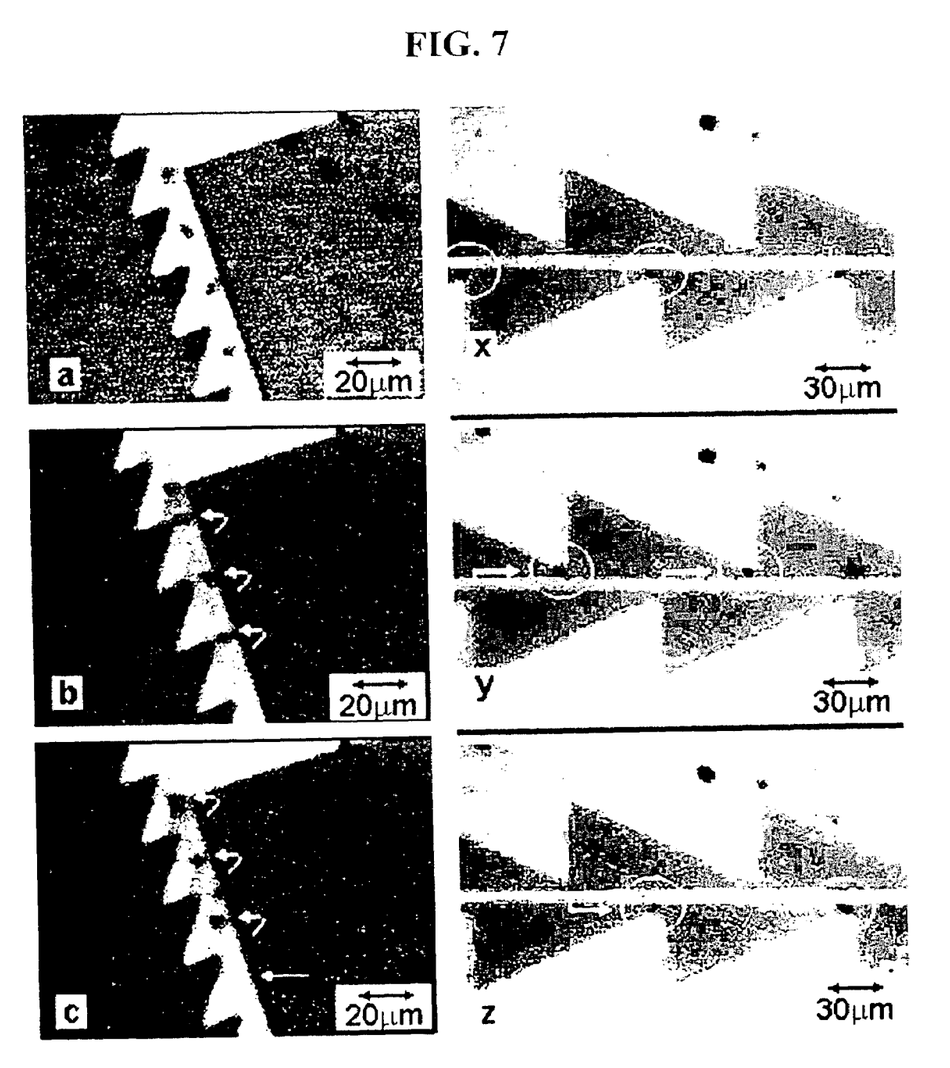
FIG. 7 shows microscopic images of single particle movement: (a), (b) and (c) show the stepwise moment of particle on a dual metallisation device and (x), (y) and (z) for a single metallisation device.

By applying a current of 50 mA alternately through the two conductors at a frequency of 0.10 Hz (a single) magnetic particle(s) can be trapped and guided step-wise along the magnetic track defined by the conductors. FIG. 7 shows a sequence of images demonstrating the movement of a single magnetic particle for both a single metallisation scheme (x, y, z) and a dual metallisation (a, b, c). FIG. 7a shows a series of magnetic beads positioned at the narrow sections of the bottom conductor while a DC-current is flowing through, while FIG. 7b shows the new position of the beads for a subsequent current pulse through the upper conductor. In FIG. 7c the current is flowing again through the bottom conductor after which one can clearly see that the magnetic beads have moved forward over a whole period.

FIGS. 7x,7y,7z show a similar sequence for the case of a single metallisation scheme.

In order to compare the transport efficiency for different structures, one can define the average speed of a magnetic bead as the distance, over which the bead is transported, divided by the minimal time needed to reach the next minimal cross-section (of the other conductor). This time can be deduced from the maximum switching frequency. For each experiment a single magnetic bead was transported in order to minimize variations in magnetic moment. As expected, increasing the current increases the average speed of the magnetic particle (illustrated in FIG. 5). An increase of the current increases the generated magnetic field and hence increases the magnetic force, which is related to the average speed.

Figure 5:
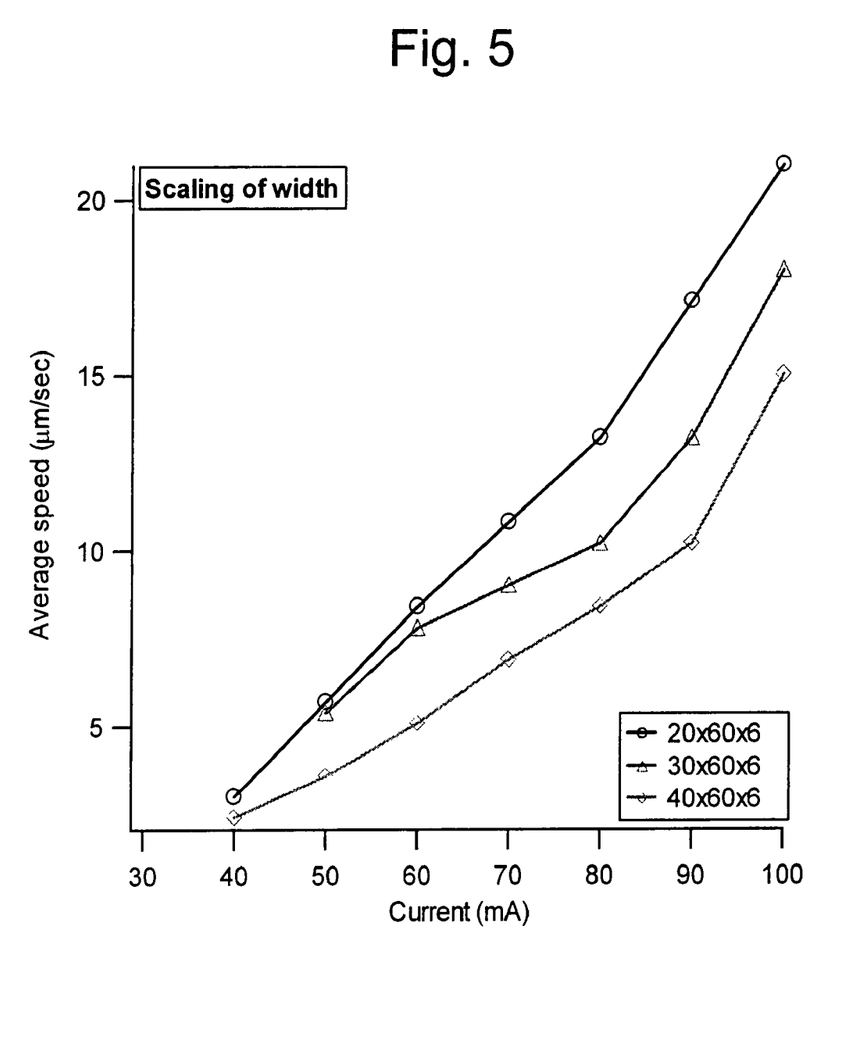
FIG. 5 shows experimental results that illustrate the relation between the average speed of the bead and the current in the current carrying structure according to a preferred embodiment of the present invention, for different values of the width of the basic structure element.

FIG. 5 also shows the influence of scaling the width of the basic triangular structure: decreasing the width results in an increase of the average speed of the magnetic particles. One may conclude that decreasing the width will decrease the magnetic field gradient and hence lower the magnetic force and average speed. However, since a decrease in the width will result in a higher average current density, it will also increase the generated magnetic field. The latter turns out to be the dominant factor.

Figure 6:
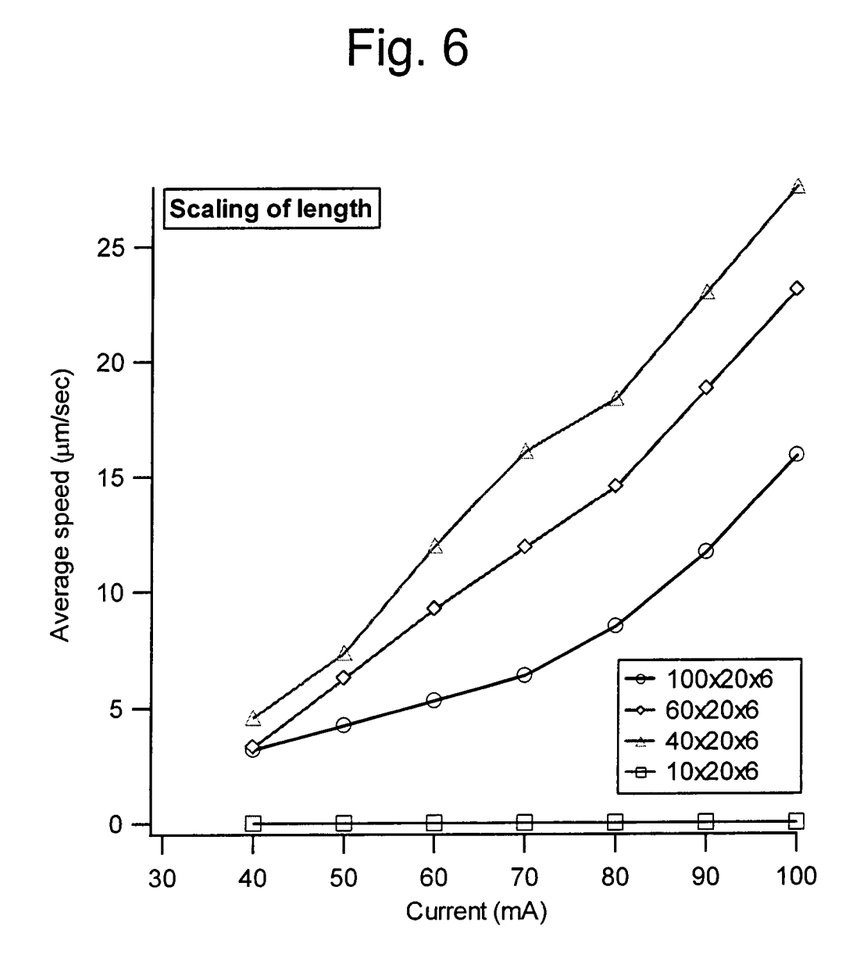
FIG. 6 shows experimental results that illustrate the relation between the average speed of the bead and the current in the current carrying structure according to a preferred embodiment of the present invention, for different values of the length of the basic structure element.

FIG. 6 shows the influence of scaling the length of the basic triangular structure. In a similar way, increasing the current results in a higher average speed. In this case, increasing the length results in a lower average speed. Again, since increasing the length decreases the magnetic field gradient, the magnetic force and the average speed are lowered. The current density is less affected and not dominant in this case.

Decreasing the length will increase the force and hence the average speed of the magnetic particle(s). However, at some point it is not possible anymore to further increase the magnetic force by only scaling down the length.

In FIG. 2, the results of this simulation for two different structures are shown.

To increase the force on a magnetic bead, one can deposit a flux-guiding material underneath the first conductor. In this way, the generated magnetic field—and hence the magnetic force—can be doubled on top of the conductor. This can either increase the magnetic force on a magnetic bead or decrease the current through the conductor and in this way, lower the heating (Joule) effect.

Experimental results prove the efficiency of such a configuration.

Both the current and the shape of the conductor will determine the switching speed and hence the overall speed of the (group of) magnetic bead(s).

FIG. 5 shows simulation results that illustrate the relation between the average speed of the bead and the current in the current carrying structure for different values of the width of the basic structure element. Results are plotted for basic structural elements with widths of 20, 30 and 40 µm, for a length of 60 µm and a thickness of 6 µm.

FIG. 6 shows simulation results that illustrate the relation between the average speed of the bead and the current in the current carrying structure for different values of respectively the length of the basic structure element. Results are plotted for basic structural elements with lengths of 10, 40, 60 and 100 µm, for a width of 20 µm and a thickness of 6 µm.

Typical currents can be between 10 and 100 mA, but higher or lower currents are not excluded.

FIG. 7 shows microscopic images of single particle movement: (a), (b) and (c) show the stepwise moment of particle on a dual metallisation device and (x), (y) and (z) for a single metallisation device.

It is to be understood that although preferred embodiments, specific constructions and configurations, as well as materials, have been discussed herein for devices according to the present invention, various changes or modifications in form and detail may be made without departing from the scope and spirit of this invention. Accordingly, the description of preferred embodiments should not be deemed to limit the scope of the present invention.

What is claimed is:

1. A method of controlling the transport of magnetic beads between a position X and position Y along a path P, the method comprising:
    applying a series of N magnetic fields having magnetic field gradients different from 0 within a predetermined proximity to the magnetic beads,
    each of the N magnetic fields being generated by providing a current to a single current-carrying structure within a plurality of current-carrying structures that are electrically isolated from each other, wherein each current-carrying structure has a non-constant charge current density along a length of the current-carrying structure in the direction of current flow when conducting a current, and wherein the series of N magnetic fields generates a series of successive field minima of magnetic fields to which the magnetic beads are attracted in forming the path P between the position X and the position Y.

2. The method according to claim 1, wherein a biological or chemical specimen is attached to one or more of the magnetic beads.

3. The method according to claim 1, wherein each of the N magnetic fields spreads over an area having dimensions of the order of about 5 to 50 times the dimension of the magnetic beads.

4. The method according to claim 1, wherein applying each of the N magnetic fields is sustained for a duration that is long enough to move at least one of the magnetic beads to a location of its substantially lowest energy in the local magnetic field.

5. The method according to claim 1, wherein at least one of the current carrying structures is disposed on a substrate by microelectronic process technology.

6. The method according to claim 1, wherein the series of N magnetic fields are generated by M current carrying structures.

7. The method according to claim 6, wherein the non-constant charge current density is generated by varying the shape of the cross-section of the current carrying structure.

8. The method according to claim 7, wherein the non-constant charge current density is generated by varying the cross-sectional surface area of the current carrying structure.

9. The method according to claim 7, wherein the non-constant charge current density is generated by varying the width of the current-carrying structure along the current direction.

10. The method according to claim 1, further comprising defining a path by a series of N locations of substantially lowest energy of the magnetic beads corresponding to the series of N magnetic fields.

11. The method according to claim 8, wherein M is 2 and wherein the local magnetic fields are generated alternately in each of the current-carrying structures.

12. The method according to claim 11, wherein the current-carrying structures are characterized by a periodic shape, formed by a repetitive structural element.

13. The method according to claim 12, wherein the structural element is characterized by an asymmetrical mirror with respect to an axis that is orthogonal to the direction of the current.

14. The method according to claim 11, wherein the M current-carrying structures are isometric.

15. The method according to claim 14, wherein the current-carrying structures are stacked on top of each other, and each is shifted by a distance different from 0 along the current direction.

16. The method according to claim 15, wherein the current carrying structures are positioned next to each other such that their respective current directions are substantially parallel and wherein each structure is shifted from the other by a distance different from 0 along the parallel direction.

17. The method according to claim 15, wherein the distance equals half the length of the basic structure element.

18. The method according to claim 12, wherein the structural element is configured to be as a shark-fin or triangular in shape.

19. The method according to claim 10, further comprising isolating, aligning and sequencing the magnetic beads based on a spatial resolution of the current-carrying structures as compared to a size of the magnetic beads.

20. The method according to claim 2, further comprising detecting and transporting the biological or chemical specimen.

21. The method according to claim 1, wherein one or more of the magnetic beads is attached to a biological specimen, and wherein the transporting the magnetic beads between position X and position Y along path P further comprises:
    transporting the biological specimen away to position Y from position X; and
    transporting the biological specimen from position Y.

22. The method according to claim 21, further comprising performing an analysis of a biochemical on the biospecimen on the specific location.

23. A method of controlling the transport of magnetic beads between a position X and position Y along a path P, the method comprising:
    providing a plurality of current-carrying structures, each structure configured to produce a non-constant charge current density along the length of the structure in the direction of current flow when conducting a current, said current-carrying structures being substantially electrically isolated from each other; and providing a current to each of said current-carrying structures to generate a series of successive field minima of magnetic fields to which the beads are attracted forming the path P between the position X and the position Y, wherein the current-carrying structures are positioned sufficiently close together to generate said series of subsequent field minima of magnetic fields.

24. The method according to claim 23, wherein at least one field minimum in one of the said structures is the result of the non-constant charge current density within the structure when conducting the current.

25. A method of controlling the transport of magnetic beads between a position X and position Y along a path P, the method comprising:

applying a series of N magnetic fields having magnetic field gradients different from 0 within a predetermined proximity to the magnetic beads; and generating each of the N magnetic fields by a single current-carrying structure, wherein each current carrying structure has a non-constant charge current density along a length of the current carrying structure in the direction of current flow when conducting a current, wherein the series of N magnetic fields are generated by M current carrying structures, and wherein the non-constant charge current density is generated by varying the cross-sectional surface area of the current carrying structure, and wherein the cross-sectional surface area decreases along the direction of the current, from one side of the structural elements to another.

* * * * *